United States Patent [19] [11] 4,190,057
Hill et al. [45] Feb. 26, 1980

[54] DEVICE FOR DETERMINING THE PATENTCY OF A BLOOD VESSEL

[75] Inventors: J. Donald Hill, San Francisco; Robert J. Harvey, Danville; David E. Downie, Lafayette, all of Calif.

[73] Assignee: Thoratec Laboratories Corporation, Berkeley, Calif.

[21] Appl. No.: 864,626

[22] Filed: Dec. 27, 1977

[51] Int. Cl.² ............................................. A61B 5/02
[52] U.S. Cl. ..................................... 128/675; 128/672
[58] Field of Search .................. 128/2 R, 2 S, 2.05 E, 128/2.05 P, 2.05 F, 2.05 V, 2.06 E, 672, 673, 675, 686, 691, 694, 774

[56] References Cited

U.S. PATENT DOCUMENTS

| 598,343 | 2/1898 | Hill et al. | 128/672 |
| 3,124,132 | 3/1964 | Sullivan et al. | 128/2.05 E |
| 3,240,207 | 3/1966 | Barker et al. | 128/2.05 E |
| 3,310,051 | 3/1967 | Schulte | 128/216 |
| 3,585,987 | 6/1971 | Svensson | 128/672 |
| 3,610,228 | 10/1971 | Temkin | 128/2.05 D |
| 3,625,199 | 12/1971 | Summers | 128/2 R |
| 4,006,735 | 2/1977 | Hittman et al. | 128/2.05 E X |
| 4,011,861 | 3/1977 | Enger | 128/2.06 E |

OTHER PUBLICATIONS

"A Nuclear Intracranial Pressure Sensor", *IEEE Trans. on Nuclear Science*, vol. 21, No. 1, Feb. 1974, pp. 697–701.

*Primary Examiner*—Richard T. Stouffer
*Attorney, Agent, or Firm*—Lothrop & West

[57] ABSTRACT

An implanted device for determining the patentcy of a transplanted vein directly connecting the aorta to transfer blood to a coronary artery has a physiologically inert bulb of flexible material disposed and retained in pressure transferring relationship to the distal region of the transplanted vein. A cuff or non-expansible sleeve surrounds the bulb and the vein and is held in position. The bulb has a single opening leading into one end of an implanted catheter. The other end of the catheter opens through a single opening in a thick-walled reservoir implanted in a subcutaneous location convenient for piercing by a hypodermic needle. At least a part of the reservoir wall is able to close upon withdrawal of the needle. The bulb, catheter and reservoir are completely filled, without distention, by an appropriate, usually isotonic, liquid. There may be a break-away connection in the catheter and various radio-opaque indicia for X-ray monitoring.

2 Claims, 8 Drawing Figures

DEVICE FOR DETERMINING THE PATENTCY OF A BLOOD VESSEL

BRIEF SUMMARY OF THE INVENTION

In order to monitor the patentcy of an implanted vein serving as a shunt between the patient's aorta and one of his coronary arteries, there is provided a bulb of physiologically inert, flexible material arranged in pressure transferring relationship with a wall of the vein. A cuff is tied around or a non-expansible sleeve surrounds both the bulb and the vein to hold them confined in position. The bulb has one opening. This leads into a remotely implanted catheter also connected preferably by a break-away fitting to an implanted, relatively thick-walled reservoir just under the skin. The bulb, catheter and reservoir are filled, without distention, with a suitable liquid. At least a part of the wall of the reservoir is susceptible to puncture by a hypodermic needle and is effective to close the puncture opening upon withdrawal of the needle. The needle is connected to a pressure indicator. Patentcy of the vein results in the reflection of both the pulsatile and steady components of the aortic pressure in the bulb of the device. This pressure is transmitted via the catheter to the reservoir. By checking the pressure in the reservoir from time to time, an observer can determine whether there is patentcy or blockage of the shunt vein. This avoids a much more elaborate and invasive checking and testing procedure presently utilized.

DETAILED DESCRIPTION

Figure 1:
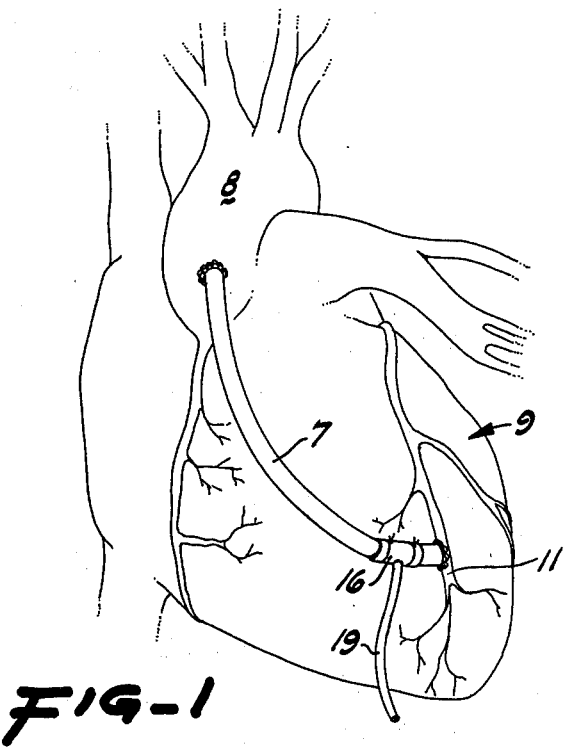
FIG. 1 is a diagram showing a patient's heart having an aortic-coronary shunt, a portion of one form of device of the invention being arranged therewith.
Figure 3:
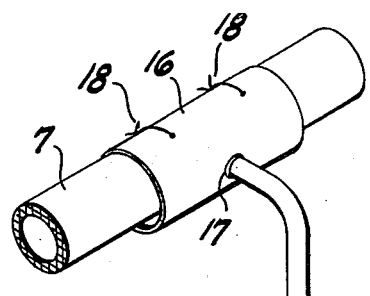
FIG. 3 is a view of a cuff and tie arrangement in its extended position.
Figure 3:
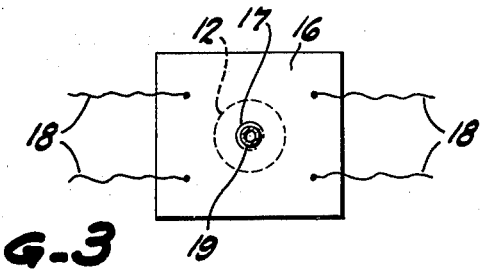
Figure 2:
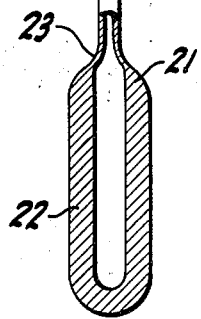
FIG. 2 is a diagram showing in detail a section of an implanted vein with one form of the device of the invention in functioning position therewith.
Figure 4:
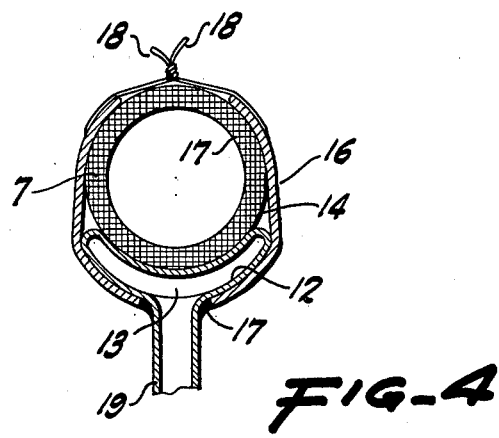
FIG. 4 is a cross-sectional view through a vein with a bulb and cuff and tie of the invention arranged thereon and showing also a part of the catheter.
Figure 5:
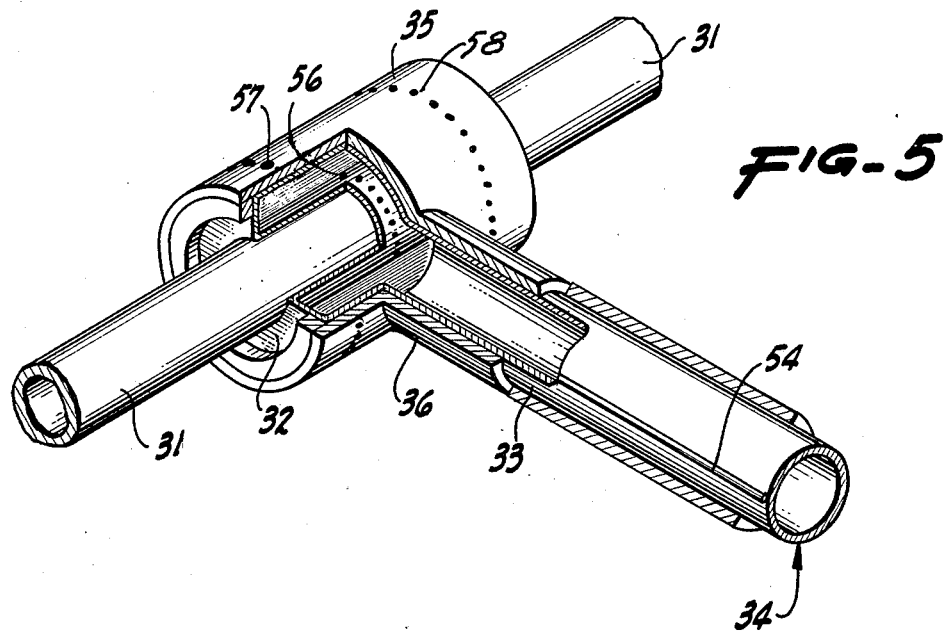
FIG. 5 is an isometric perspective view of a portion of a vein with another form of device pursuant to the invention installed thereon, certain portions being in cross-section.
Figure 6:
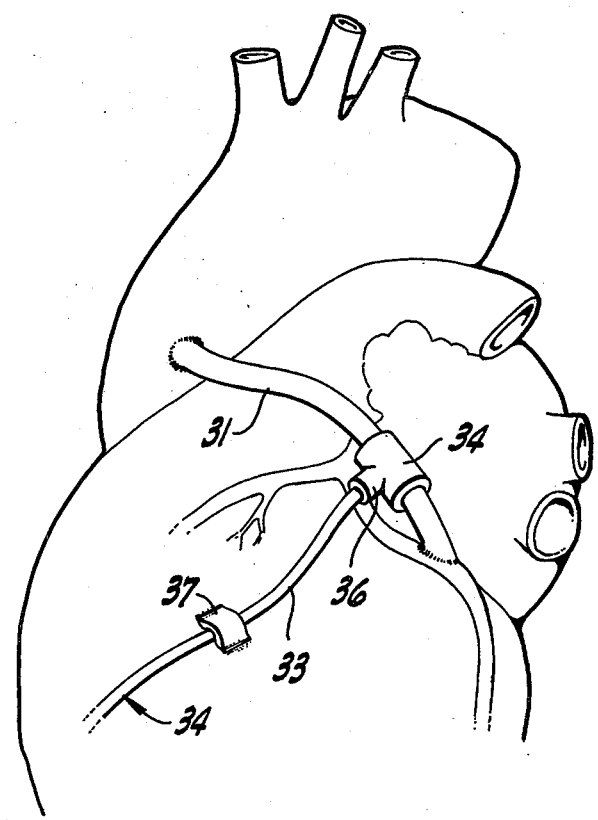
FIG. 6 is a view similar to FIG. 1 but showing the second form of the device of the invention, portions of the figure being broken away to reduce its size.

Since heart surgery has become an effective life-sustaining procedure, there has grown up a practice of providing bypasses or shunts leading from the aorta to a particular coronary artery or arteries. The shunts are effective when they operate satisfactorily, but since they are subject to blocking or occlusion for various reasons, it is necessary that their effectiveness or openness be checked from time to time. This has heretofore been accomplished, according to one technique, by threading a catheter from outside the body through a major artery (femoral) into the heart itself; introducing a radio-opaque dye; and then observing by X-ray the propagation of the dye. This is a relatively expensive, uncomfortable procedure with an accompanying risk for the patient. In some patients it has to be accomplished repeatedly.

It is therefore an object of the invention to provide a less traumatic, less expensive and at least equally or more effective device for easily indicating the patentcy of a bypass or a shunt blood vessel.

While techniques and mechanisms may vary from time to time, two forms of procedure and mechanism are set out below. A patient has a shunt blood vessel 7 extending from a connection to the aorta 8 of his heart 9 and extending to a connection to one of the coronary blood vessels 11 of his heart. At the time of the initial bypass or shunt operation we also provide a suitable patentcy indicating device. Customarily, the blood vessel 7 is a vein that has been removed from another portion of the patient's body (e.g. his leg) and has been implanted and connected substantially as described.

At the time of the implant and connection of the vein to the aorta and a coronary vessel, a bulb 12 is preferably provided at the distal end of the bypass or shunt vessel 7. The bulb is an enclosure having a single opening 13 therein. The bulb is made of physiologically inert, somewhat flexible and perhaps elastic but not greatly stretchable material; for example, an appropriate polyether urethane or silicone rubber substance. Any such substance compatible with body fluids and surrounding tissue is acceptable. The bulb may be initially flat or may have a partially arcuate cross-section in one view so as to conform reasonably well with the normal shape of the wall 14 of the blood vessel 7.

Preferably also, the bulb is held in pressure transferring relationship with the blood vessel wall 14 by being paired or nested therewith. This is accomplished by a flexible cuff 16 of physiologically compatible material of generally rectangular plan when flat and having an opening 17 therein. The cuff may be reinforced around the margin of the opening. The cuff is also provided with attached or integral ties 18, preferably at both ends. The cuff is wrapped around both the bulb and the touching blood vessel and is held inexpansibly in position by securing the ties 18 in the customary way.

Adapted to communicate with the opening 17 and as a virtually integral portion of the bulb is a physiologically inert, flexible and perhaps elastic but not greatly stretchable catheter 19 of a relatively small internal diameter; for example, one thirty-second inch. The catheter and the bulb are sealed together or initially formed integrally so that there is no leakage around the bulb opening. The catheter is designed to be implanted in the patient's body and to extend from the region of the heart and the location of the bulb on the vein 7 to a convenient and safe location for subsequent scrutiny, preferably just under the skin, say, near the patient's waist.

The end of the catheter away from the blood vessel is substantially integral with the wall 21 of a reservoir 22. The reservoir is closed entirely except for a single opening 23 communicating with the end of the catheter. The reservoir likewise is of an innocuous material and has a relatively thick wall. The generally closed assemblage of the bulb, the catheter and the reservoir is completely filled, without appreciable distention, preferably by a biocompatible isotonic liquid effective to transmit pressure between the bulb and the reservoir and to minimize net fluid movement between the assemblage and the patient resulting from, for example, osmotic processes.

When this bulb-catheter-reservoir assemblage has been implanted in the patient, a check of the patentcy of the shunt vessel 7 can readily be made by the physician. His procedure can be performed on an out-patient or even on an office visit basis. He inserts a hypodermic needle subcutaneously and through the thick wall 21 to the interior of the reservoir 22. The hypodermic needle, while inserted, is connected to any appropriate kind of external pressure monitoring instrument.

If the shunt or bypass vessel 7 is patent and blood is flowing and pulsing therethrough as it should be, the pulsations are picked up by the bulb and transmitted through the catheter to the interior of the reservoir. They are then transmitted to the external indicating device. The external monitoring instrument affords an indication of the vein pressurization. If, however, there is no or substantially no external indication of pressure fluctuation, then it must be assumed that the bypass vessel is occluded and is not effective. Remedial measures can then be taken.

Since it is advisable to perform the monitoring procedure even in satisfactory cases and to do so at reasonable intervals, the thick wall of the reservoir permits multiple piercing by the hypodermic needle. The thick wall also has the beneficial property of being self-closing and nonleaking when the needle is withdrawn. In this way the implanted reservoir can serve for a number of individual examinations.

Some patients have more than one bypass or shunt blood vessel extending from the aorta to different, individual coronary arteries. It is possible, because of the small extent, minimum bulk and absence of invasive detriment of the present arrangement, to implant several bulbs, cuffs, catheters and reservoirs in one patient, each reservoir being at an accessible point in the patient's body and each implantation being an individual system for a particular bypass vessel. Careful records can be kept of the source and terminal location of each closed system.

All of the components of each arrangement are inert and are readily packaged. Each individual system can be supplied in sterile condition for immediate availability during a bypass operation. In the event of multiple reservoirs, it is preferred to provide some identification means on each one. The patient's record can show which reservoir is responsive to which by-pass vessel bulb.

In a related arrangement, as shown in FIGS. 5 through 8, the implanted, shunt or bypass vein 31 is threaded through or surrounded by a bulb 32 or cuff of annular form having closed ends. The material of the bulb is as before, being closely responsive to movement of the vein wall and being substantially resistant to net movement of isotonic fluid between the components of the monitor and the patient. The bulb is formed integrally with or is attached to one end portion 33 of a catheter 34. A convenient construction for the catheter is a small-bore (almost capillary) tube of polyethylene tubing sheathed in a Silastic tube.

Disposed around the bulb is a sleeve 35 or wrap of tubular form and of substantially non-distensible character. There is a smoothly merging, tubular branch 36 on the wrap arranged around the catheter at the junction of the bulb and the catheter. A Silastic seal may be applied at this point. The catheter 34 may have a suture pad 37 near the sleeve and can continue directly to a reservoir 38 corresponding to the reservoir 22. The reservoir 38 comprises a relatively rigid body closed except for connection to the other end portion 39 of the catheter 34. The reservoir incorporates in its wall and protects a self-sealing, flexible membrane 41 disposed just beneath the patient's skin.

Figures 7, 8:
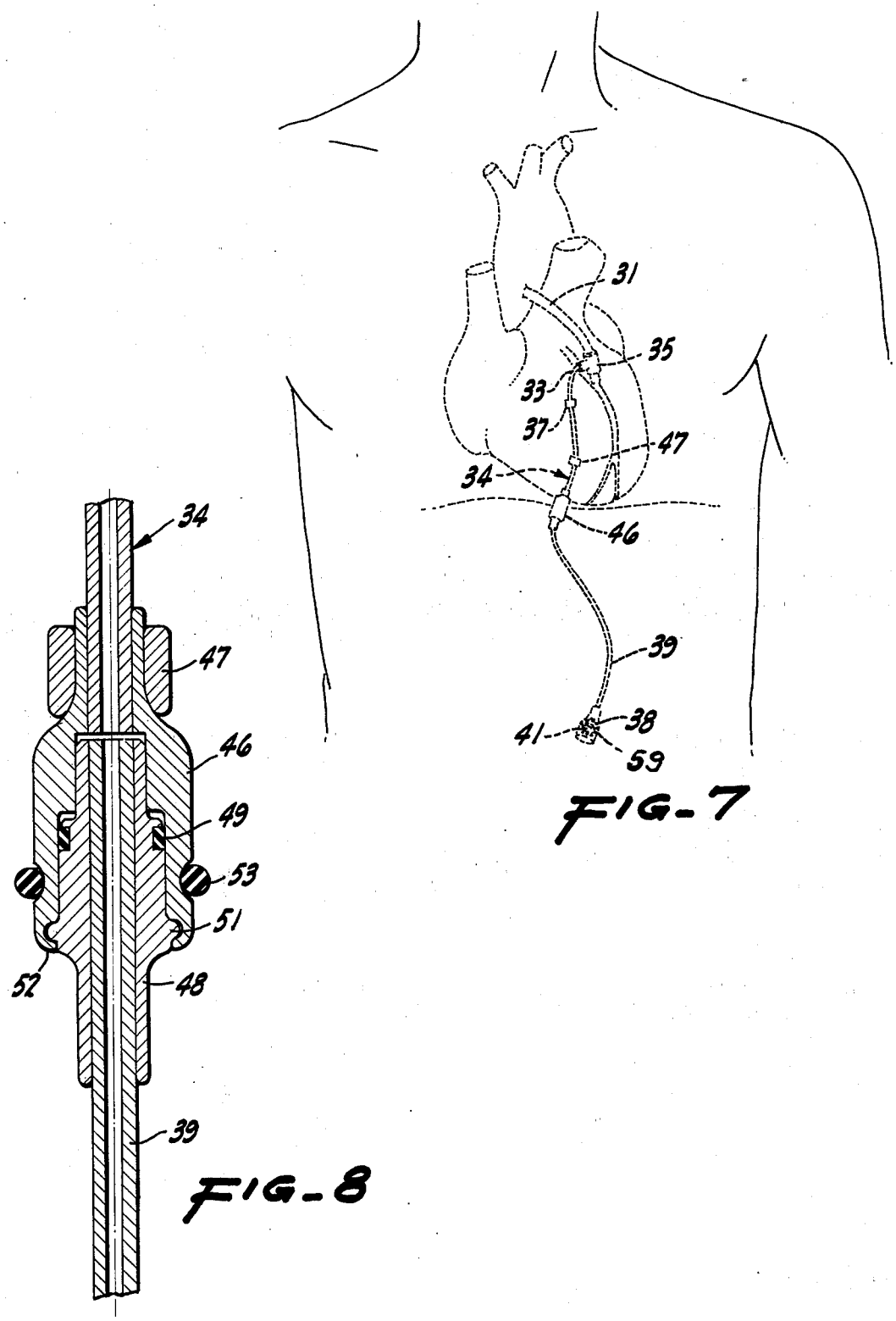
FIG. 7 is a view of part of a torso with a device pursuant to the invention implanted therein.
FIG. 8 is an axial cross-section of one form of break-away device usable with the catheter.

While, as indicated, in many instances the catheter can be a continuous tube, there are sometimes reasons to make the catheter easily and quickly disconnectable at a convenient location; for example, near the patient's diaphragm. A quick or self-acting break-away coupling, as shown in FIGS. 7 and 8, may be used. This comprises a female fitting 46 held in location by a suture pad 47. The fitting 46 immediately engages the catheter end portion 39. Detachably engaging the fitting 46 is a male fitting 48 firmly joined to the catheter end portion 39. A sealing O-ring 49 precludes leakage between the fittings. The male fitting has a peripheral bead 51 encompassed by an elastic or flexible rim 52 on the female fitting. A constricting spring such as an elastic O-ring retainer 53 around the female fitting assists in biasing the interengagement of the bead and rim. The total bias is preferably such that the fittings are normally held tightly together but part upon the imposition of a predetermined, axial separating force. A catheter parting at this point is substantially harmless and avoids the imposition of excessive and possibly seriously detrimental forces on other parts of the implant. Any loss of fluid is not harmful and is slight because of the nearly capillary size of the catheter. A fine wire 54 opaque to X-rays or comparable radiation is incorporated in the catheter so that any break at the fittings 46 and 48, or elsewhere, can readily be observed by fluoroscopy or X-ray.

Pulsations due to pressure changes in the bypass vein can be easily detected as pulses of the diaphragm 41. Also, the actual pressure may be measured by inserting a needle percutaneously through the diaphragm 41 and joining the needle to any suitable pressure indicating or recording device.

Certain portions of implant may be especially treated. For example, the suture pad 37, the sleeve 35 and its tubular branch 36, and the first two centimeters of the catheter end portion 33 may be silicone coated so that a smooth fluid-filled capsule will develop around the vein and the cuff and the local portion of the catheter. The rest of the catheter 34 and the reservoir 38 can be prepared with any of a number of surfaces, such as microporous material, which allow a firm tissue ingrowth to surround and fix the device in place.

For various reasons, it may be decided in an individual case to inflate the bulb or cuff 32 only at surgery and at checking times and to leave the system substantially drained at all other times. To assist in accurate reinflation at checking, rings 56, 57 and 58 can be provided as desired on the bulb and the sleeve. The rings are opaque to X-rays. Their relative position is noted at surgery and is reproduced by reinflation at any subsequent followup.

A similar marker 59 is preferably provided in the reservoir 38 surrounding the slightly recessed membrane 41 to assist in subsequent needle perforation.

During routine office visits, the physician can feel the pressure pulses in the reservoir located subcutaneously with his fingers. This is not unlike the procedures now used to determine heart rate by feeling the pressure pulses in the arteries of the wrist. The device provides a simple, non-traumatic means of ascertaining at least qualitative information on the patentcy (or lack of patentcy) of the A-C shunts.

In this form of device, the bulb is especially well located against dislodgment. Volume changes therein are directly transmitted with little loss due to the non-expansible confining sleeve or wrap. The break-away fitting is a safeguard especially in case of accident, and the substantially non-extensible reservoir causes pressure changes to be almost entirely responded to by the relatively flexible membrane 41. There is thus provided a safe, accurately responsive pressure indicator for monitoring and checking the patentcy of a shunt or vein bypass in the heart region.

We claim:

1. A device for determining the patentcy of a blood vessel comprising a physiologically inert, implantable flexible bulb closed except for a first opening; inexpansible means for securing said bulb in motion transferring relationship to the wall of a blood vessel; a physiologically innocuous, implantable reservoir closed except for a second opening; and a physiologically inert, implantable catheter at one end secured to said bulb and communicating therewith through said first opening and at the other end secured to said reservoir and communicating therewith through said second opening, said reservoir having a wall which is made of a material having the property of permitting the passage therethrough of a hypodermic needle and having the property of self-sealing upon the withdrawal therefrom of a hypodermic needle.

2. A device as in claim 1 in which said device is for determining the patentcy of a blood vessel which is a transplanted vein adapted to be connected to the aorta and a coronary artery and adapted to conduct blood from the aorta to said coronary artery and said bulb is adapted to be disposed adjacent the distal end of said blood vessel.

* * * * *